US011642360B2

(12) United States Patent
Ramey et al.

(10) Patent No.: US 11,642,360 B2
(45) Date of Patent: May 9, 2023

(54) COMPOSITIONS FOR IMPROVING JOINT HEALTH

(71) Applicant: BioRelief, LLC, Lexington, KY (US)

(72) Inventors: Gary Jeffery Ramey, Cambridge, MA (US); V. A. Shiva Ayyadurai, Cambridge, MA (US); Prabhakar Deonikar, Cambridge, MA (US)

(73) Assignee: BioRelief, LLC, Lexington, KY (US)

( * ) Notice: Subject to any disclaimer, the term of this patent is extended or adjusted under 35 U.S.C. 154(b) by 0 days.

(21) Appl. No.: 17/011,838

(22) Filed: Sep. 3, 2020

(65) Prior Publication Data

US 2021/0060048 A1    Mar. 4, 2021

Related U.S. Application Data

(60) Provisional application No. 62/895,292, filed on Sep. 3, 2019.

(51) Int. Cl.
*A61K 31/7048* (2006.01)
*A61P 19/02* (2006.01)
*A61P 29/00* (2006.01)
*A61K 31/355* (2006.01)

(52) U.S. Cl.
CPC ........ *A61K 31/7048* (2013.01); *A61K 31/355* (2013.01); *A61P 19/02* (2018.01); *A61P 29/00* (2018.01)

(58) Field of Classification Search
CPC ... A61K 31/7048; A61K 31/355; A61P 19/02; A61P 29/00
USPC ........................................................ 514/27
See application file for complete search history.

(56) References Cited

U.S. PATENT DOCUMENTS

2007/0154540 A1*    7/2007    Park ...................... A23L 33/105
                                                                424/451

FOREIGN PATENT DOCUMENTS

WO    WO-2013186220 A1 * 12/2013

OTHER PUBLICATIONS

Hughes et al. (Reviews in Food Science and Nutrition, 57 (17). pp. 3601-3613 (2017)).*
Sakata et al. (Cancer Letters 199 (2003) 139-145).*
Lee et al. (Arch Pharm Res vol. 30, No. 10, 1318-1327, 2007).*
Walsh et al. (Br J Clin Pharmacol, 80:5, 965-978 (20150).*
Engler et al. (Biochemical and Biophysical Research Communications 359 (2007) 884-888).*
Ayyadurai and Deonikar, "Do GMOs Accumulate Formaldehyde and Disrupt Molecular Systems Equilibria? Systems Biology May Provide Answers", Jul. 10, 2015, Agricultural Sciences, 6:630-662.
Ayyadurai and Forbes-Dewey Jr., "CytoSolve: A Scalable Computational Method for Dynamic Integration of Multiple Molecular Pathway Models", Cellular and Molecular Bioengineering, Mar. 2011, 4:28-45.
Ayyadurai, "Scalable Computational Architecture for Integrating Biological Pathway Models," Doctoral Dissertation, Massachusetts Institute of Technology, 2007, 321 pages.
Avyadurai, "Services-Based Systems Architecture for Modeling the Whole Cell: A Distributed Collaborative Engineering Systems Approach," Communications in Medical and Care Compunetics, 2011, 1:115-168.
Delgado et al., "Validation of digital visual analog scale pain scoring with a traditional paper-based visual analog scale in adults," Journal of the American Academy of Orthopaedic Surgeons, Global Research & Reviews, Mar. 2018, 6 pages.
Felson et al., "A proposed revision to the ACR20: the hybrid measure of American College of Rheumatology response," Arthritis Care & Research, Mar. 15, 2007, 57(2):193-202.
Gordillo-Moscoso et al., "Relationship between serum levels of triglycerides and vascular inflammation, measured as COX-2, in arteries from diabetic patients: a translational study", Lipids Health Disease, Mar. 2018, 9 pages.
Hirata et al., "Kinetics of radical-scavenging activity of hesperetin and hesperidin and their inhibitory activity on COX-2 expression", Anticancer Research, Sep. 2005, 8 pages.
Inoue et al., Inhibition of COX-2 expression by topical diclofenac enhanced radiation sensitivity via enhancement of Trail in human prostate adenocarcinoma xenograft model, BMC Urology, Jan. 5, 2013, 9 pages.
Koo et al., "In silico modeling of shear-stress-induced nitric oxide production in endothelial cells through systems biology," Biophysical journal, May 21, 2013, 104(10):2295-2306.
Neugebauer et al., "Techniques for assessing knee joint pain in arthritis", Molecular Pain, Mar. 28, 2007, 13 pages.
Nordsletten et al. "Multiscale Mathematical Modeling to Support Drug Development", IEEE Trans BiomedEng., Oct. 24, 2011, 5 pages.
Pavelescu "On reactive oxygen species measurement in living systems," Journal of medicine and life, 2015, 8(Spec Issue):38-42.
Sweeney et al., "Pericytes of the neurovascular unit: key functions and signaling pathways," Nature neuroscience, Jun. 2016, 19(6):771-783.
Wang et al., "Growth and adherence of *Staphylococcus aureus* were enhanced through the PGE2 produced by the activated COX-2/PGE2 pathway of infected oral epithelial cells," PLoS One, May 4, 2017, 12(5):e0177166, 21 pages.

(Continued)

*Primary Examiner* — Shaojia A Jiang
*Assistant Examiner* — Michael C Henry
(74) *Attorney, Agent, or Firm* — Oblon, McClelland, Maier & Neustadt, L.L.P.

(57) ABSTRACT

The present disclosure is related to dietary supplements. For example, this disclosure relates to compositions that include, for example, one or more agents that decrease the concentration of cyclooxygenase-2, decrease the concentration of transient receptor potential cation channel subfamily V member 1, and/or decrease calcitonin gene-related peptide concentration. In some embodiments, a composition as provided herein includes apigenin present in an amount of about 1% to about 5% w/w of the composition; and hesperidin present in an amount of about 90% to about 99% w/w of the composition. Such compositions are useful for decreasing joint pain and/or inflammation.

9 Claims, 5 Drawing Sheets

(56) References Cited

OTHER PUBLICATIONS

Wu et al., "Evaluation of the post-treatment anti-inflammatory capacity of osteoarthritic chondrocytes: An in vitro study using baicalein," Regenerative therapy, Jun. 1, 2020, 14:177-183.
Yang et al., "Involvement of TRPV1 in the expression and release of calcitonin gene-related peptide induced by rutaecarpine", Mol Med Rep., Apr. 2018, 17(4): 5168-5174.

* cited by examiner

COMPOSITIONS FOR IMPROVING JOINT HEALTH

CROSS-REFERENCE TO RELATED APPLICATIONS

This application claims the benefit of U.S. Provisional Application No. 62/895,292, filed Sep. 3, 2019, the contents of which are hereby incorporated by reference.

TECHNICAL FIELD

This disclosure is related to the field of dietary supplements. For example, this disclosure relates to compositions useful for improving or decreasing joint pain and/or joint inflammation. Such compositions can include, for example, one or more agents that decrease the concentration of cyclooxygenase-2, decrease the concentration of transient receptor potential cation channel subfamily V member 1, and/or decrease calcitonin gene-related peptide concentration.

BACKGROUND

Joint issues, such as pain and/or inflammation, are extremely common. In a National Health Interview Survey, about one-third of adults reported having joint pain within the past 30 days. Joint pain can include discomfort, pain, or inflammation and can arise from any part of a joint such as cartilage, bone, ligaments, tendons, or muscles. Most commonly, joint pain refers to arthritis or arthralgia, which is inflammation and/or pain from within the joint itself. In the United States, it is estimated that 23% of all adults have arthritis, and osteoarthritis, which affects nearly 27 million Americans, is one of the most common reasons for severe hip or knee pain.

Currently, there are many treatments recommended for relieving joint pain and inflammation. For example, non-steroidal anti-inflammatory drugs (NSAIDs) are frequently used to treat joint pain and inflammation. Although NSAIDs can relieve some joint stiffness, inflammation, and pain, NSAIDs can also lead to side effects such as gastric bleeding, liver damage, and kidney damage.

SUMMARY

Provided herein are methods for decreasing joint inflammation in a subject in need thereof comprising administering to the subject a composition comprising two or more agents that decrease the concentration of cyclooxygenase-2 (COX-2). Also provided herein are methods for improving joint inflammation in a subject in need thereof comprising administering to the subject a composition comprising two or more agents that decrease the concentration of cyclooxygenase-2 (COX-2).

In some embodiments, the joint inflammation is associated with one or more of: an injury, ankylosing spondylitis, bursitis, gout, juvenile rheumatoid arthritis, lupus, Lyme disease, osteoarthritis, pseudogout, psoriatic arthritis, rheumatoid arthritis, and tendonitis. In some embodiments, the injury is a broken bone, a dislocation, a sprain, or a strain.

In some embodiments, at least one agent that decreases the concentration of COX-2 also decreases prostaglandin $E_2$ ($PGE_2$) concentration. In some embodiments, at least one agent that decreases the concentration of COX-2 also decreases reactive oxygen species (ROS) concentration.

In some embodiments, at least one agent that decreases the concentration of COX-2 modulates COX-2 synthesis. In some embodiments, at least one agent that decreases the concentration of COX-2 decreases COX-2 expression. In some embodiments, at least one agent that decreases the concentration of $PGE_2$ modulates arachidonic acid metabolism. In some embodiments, at least one agent that decreases the concentration of ROS modulates an oxidative stress pathway.

In some embodiments, the two or more agents that decrease COX-2 concentration comprise: a flavone; and a flavanone.

Also provided herein are methods for decreasing joint pain in a subject in need thereof comprising administering to the subject a composition comprising two or more agents that decrease the concentration of transient receptor potential cation channel subfamily V member 1 (TRPV1); decrease the concentration of calcitonin gene-related peptide (CGRP); or a combination thereof. Also provided herein are methods for improving joint pain in a subject in need thereof comprising administering to the subject a composition comprising two or more agents that decrease the concentration of transient receptor potential cation channel subfamily V member 1 (TRPV1); decrease the concentration of calcitonin gene-related peptide (CGRP); or a combination thereof.

In some embodiments, the joint pain is associated with one or more of: an injury, adult Still's disease, ankylosing spondylitis, avascular necrosis, bone cancer, bursitis, complex regional pain syndrome, fibromyalgia, gonococcal arthritis, gout, hypothyroidism, juvenile idiopathic arthritis, leukemia, lupus, Lyme disease, osteoarthritis, osteomyelitis, Paget's disease of bone, polymyalgia rheumatic, pseudogout, psoriatic arthritis, reactive arthritis, rheumatic fever, rheumatoid arthritis, rickets, sarcoidosis, septic arthritis, and tendinitis. In some embodiments, the injury is a broken bone, a dislocation, a sprain, or a strain.

In some embodiments, at least one agent also modulates PGE2 signaling.

In some embodiments, the two or more agents that decrease the concentration of TRPV1; decrease the concentration of CGRP; or a combination thereof, comprise: a flavone and a flavanone.

In some of any of the above embodiments, the flavanone is a trihydroxyflavanone.

In some embodiments, the trihydroxyflavanone is selected from the group consisting of: hesperidin, butin, garbanzol, naringenin, pinobanksin, and a combination thereof.

In some embodiments, the flavanone is hesperidin.

In some embodiments, the flavanone is present in an amount of about 30% to about 99% w/w of the composition. In some embodiments, the flavanone is present in an amount of about 50% to about 98% w/w of the composition. In some embodiments, the flavanone is present in an amount of about 70% to about 98% w/w of the composition. In some embodiments, the flavanone is present in an amount of about 97% w/w of the composition.

In some embodiments, the flavone is a trihydroxyflavone. In some embodiments, the trihydroxyflavone is selected from the group consisting of: apigenin, baicalein, norwogonin, galangin, and a combination thereof.

In some embodiments, the flavone is apigenin.

In some embodiments, the flavone is present in an amount of about 0.01% to about 50% w/w of the composition. In some embodiments, the flavone is present in an amount of about 0.1% to about 30% w/w of the composition. In some embodiments, the flavone is present in an amount of about 1% to about 20% w/w of the composition. In some embodiments, the flavone is present in an amount of about 2% to about 10% w/w of the composition. In some embodiments, the flavone is present in an amount of about 3% w/w of the composition.

In some embodiments, the flavanone is hesperidin and the flavone is apigenin.

In some embodiments, the composition comprises: about 0.01% to about 30% w/w of the composition of apigenin; and about 30% to about 99% w/w of the composition of hespiridin;

In some embodiments, the composition comprises: about 3% w/w of the composition of apigenin; and about 97% w/w of the composition of hespiridin.

In some embodiments, the composition further comprises one or more excipients, diluents, or carriers.

In some embodiments, the composition is administered orally.

In some embodiments, the joint is a foot joint, a knee joint, a hip joint, a sacroiliac joint, a temporomandibular joint, a facet joint, a sternoclavicular joint, a shoulder joint, an acromioclavicular joint, a wrist joint, an elbow joint, a carpometacarpal joint, an intermetacarpal articulation, a metacarpophalangeal joint, an interphalangeal joint of the hand.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
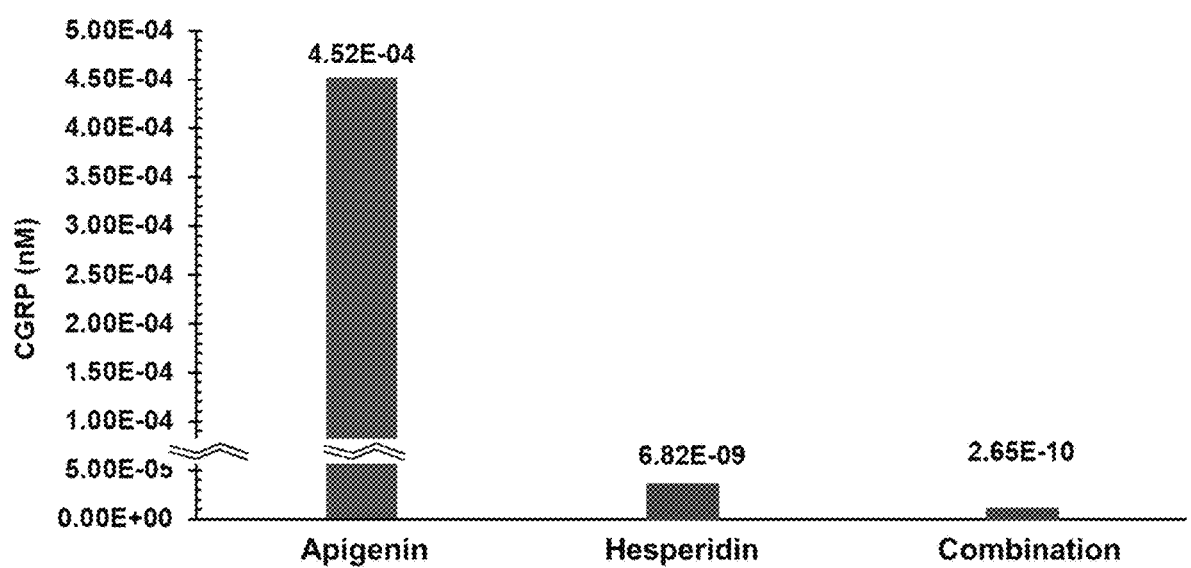
FIG. 1 is a bar graph comparing the concentration of calcitonin gene-related peptide (CGRP) for apigenin, hesperidin, and a combination of apigenin and hesperidin versus a control (data not shown, the concentration of CGRP for the control was 0.045 nM). The plot is based on a biomolecular computational model using CytoSolve® and modeling mechanisms of the CGRP signaling pathway.

Joint pain can include discomfort, pain, or inflammation arising from any part of a joint such as cartilage, bone, ligaments, tendons, or muscles, but joint pain often refers to arthritis or arthralgia, which is inflammation and/or pain from within the joint itself. For example, the synovium and joint capsule are major sources of pain within a joint, and the synovial membrane is the main site affected by inflammation (synovitis). Joint inflammation can occur with injury, disease, and/or infection.

Non-steroidal anti-inflammatory drugs (NSAIDs) are frequently used to treat joint pain and/or inflammation. However, NSAIDs can also lead to side effects such as gastric bleeding, liver damage, and kidney damage. Ibuprofen is a non-selective, reversible inhibitor of the cyclooxygenase (COX) enzymes, COX-1 and COX-2 and only modulates one mechanism of action (arachidonic acid metabolism) that is involved in joint inflammation and pain. COX-1 is involved in mucus secretion in the stomach, which protects the stomach from the acidic environment. By non-specifically inhibiting COX-1, ibuprofen can promote erosion of stomach lining and development of stomach ulcers. On the other hand, the compositions as described herein are selective COX-2 modulators. As such, the compositions as described herein do not have the same side effect of stomach ulceration as that of ibuprofen. Moreover, the compositions of the present disclosure can modulate four different mechanisms of action involved in joint pain and inflammation including arachidonic acid metabolism, PGE2 signaling, COX-2 synthesis, and oxidative stress whereas ibuprofen only modulates PGE2 signaling.

Accordingly, the present disclosure provides methods and compositions (e.g., dietary supplements) related to reducing joint pain and/or joint inflammation. Such compositions can contain two or more agents that decrease the concentration of cyclooxygenase-2, decrease the concentration of transient receptor potential cation channel subfamily V member 1, decrease calcitonin gene-related peptide concentration, or a combination thereof, useful for reducing or improving joint pain and/or joint inflammation.

Definitions

As used herein, the phrase "joint pain is associated with" or "joint inflammation is associated with" a disease, disorder, or condition encompasses a subject with joint pain or joint inflammation that has also been diagnosed with, was previously diagnosed with, or has symptoms associated with the disease, disorder, or condition.

As used herein, the phrases an "effective amount" or a "therapeutically effective amount" of an active agent or ingredient, or pharmaceutically active agent or ingredient, refer to an amount of the active agent sufficient enough to reduce or eliminate one or more symptoms of the disorder or to effect a cure upon administration. Effective amounts of the active agent will vary with the kind of active agent chosen, the particular condition or conditions being treated, the severity of the condition, the duration of the treatment, the specific components of the composition being used, and like factors.

As used herein, "subject" refers to any subject, particularly a mammalian subject, for whom diagnosis, prognosis, or therapy is desired, for example, a human.

Reference to the term "about" has its usual meaning in the context of compositions to allow for reasonable variations in amounts that can achieve the same effect and also refers herein to a value of plus or minus 10% of the provided value. For example, "about 20" means or includes amounts from 18 to and including 22.

As used herein, a "treatment" or "treating" of a disease, disorder, or condition encompasses alleviation of at least one symptom thereof, a reduction in the severity thereof, or the delay or inhibition of the progression thereof. Treatment need not mean that the disease, disorder, or condition is totally cured. A useful composition herein needs only to reduce the severity of a disease, disorder, or condition, reduce the severity of one or more symptoms associated therewith, or provide improvement to a patient or subject's quality of life.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. As used herein, the singular form "a", "an", and "the" include plural references unless indicated otherwise. For example, "an" excipient includes one or more excipients. It is understood that aspects and variations of the invention described herein include "consisting of" and/or "consisting essentially of" aspects and variations.

Agents that Decrease the Concentration of Cyclooxygenase-2 (COX-2)

In some embodiments, a composition as described herein can comprise an agent that decreases the concentration of COX-2. For example, in some embodiments, an agent that decreases the concentration of COX-2 is an agent that decreases COX-2 synthesis. As another example, an agent that decreases the concentration of COX-2 can be an agent that decreases COX-2 expression. Many agents that decrease the concentration of COX-2 are known to one of skill in the art. Non-limiting examples of an agent that decreases the concentration of COX-2 include hesperidin and apigenin. Several methods for measuring COX-2 concentration are known to one of ordinary skill in the art. Non-limiting examples of such methods include: measuring COX-2 mRNA using RT-PCR or Northern blot and measuring COX-2 protein using Western blot (see, for example, Inoue et al. *BMC Urol.* 2013 Jan. 5; 13:1; Hirata et al. *Anticancer Res.* 2005 September-October; 25(5):3367-74; and Gordillo-Moscoso et al. *Lipids Health Dis.* 2013 May 3; 12:62; each of which are incorporated by reference herein in their entireties).

In some embodiments, an agent that decreases the concentration of COX-2 decreases the concentration of COX-2 by at least 0.5%, 1%, 5%, 10%, or 15%. For example, the agent that decreases the concentration of COX-2 decreases the concentration of COX-2 by about 1%, about 2%, about 3%, about 4%, about 5%, about 10%, about 15% or more.

In some embodiments, an agent that decreases COX-2 concentration also decreases prostaglandin $E_2$ ($PGE_2$) concentration. In some embodiments, the agent that also decreases $PGE_2$ concentration modulates arachidonic acid metabolism. Several methods for measuring $PGE_2$ concentration are known to one of ordinary skill in the art. Non-limiting examples of such methods include: measuring $PGE_2$ protein using ELISA (see, for example, Wang et al. *PLoS One.* 2017; 12(5): e0177166; which is incorporated by reference herein in its entirety).

In some embodiments, an agent that decreases COX-2 concentration also decreases reactive oxygen species (ROS) concentration. In some embodiments, the agent also decreases ROS concentration modulates an oxidative stress pathway. Several methods for measuring ROS concentration are known to one of ordinary skill in the art. Non-limiting examples of such methods include the methods described in Pavelescu. *J Med Life.* 2015; 8(Spec Issue): 38-42, which is incorporated by reference herein in its entirety.

In some embodiments, an agent that decreases COX-2 concentration is present in a composition as described herein in an amount of about 30% to about 100% w/w of the composition. For example, an agent that decreases COX-2 concentration can be present in a composition as described herein in an amount of about 30% to about 40%, about 30% to about 50%, about 30% to about 60%, about 30% to about 70%, about 30% to about 80%, about 30% to about 90%, about 90% to about 100%, about 80% to about 100%, about 70% to about 100%, about 60% to about 100%, about 50% to about 100%, about 40% to about 100%, or about 50% to about 100%, w/w of the composition.

In some embodiments, an agent that decreases COX-2 concentration is a flavone. In some embodiments, an agent that decreases COX-2 concentration is a flavanone.

Agents that Decrease Transient Receptor Potential Cation Channel Subfamily V Member 1 (TRPV1) Concentration In some embodiments, a composition as described herein can comprise an agent that decreases the concentration of TRPV1. For example, in some embodiments, an agent that decreases the concentration of TRPV1 is an agent that decreases TRPV1 synthesis. As another example, an agent that decreases the concentration of TRPV1 can be an agent that decreases TRPV1 expression. Many agents that decrease the concentration of TRPV1 are known to one of skill in the art. Non-limiting examples of an agent that decreases the concentration of TRPV1 include hesperidin and apigenin. Several methods for measuring TRPV1 concentration are known to one of ordinary skill in the art. Non-limiting examples of such methods include: measuring TRPV1 mRNA using RT-qPCR or Northern blot (see, for example, Yang et al. *Mol Med Rep.* 2018 April; 17(4): 5168-5174, which is incorporated by reference herein in its entirety).

In some embodiments, an agent that decreases the concentration of TRPV1 decreases the concentration of TRPV1 by at least 0.5%, 1%, 5%, 10%, or 15%. For example, the agent that decreases the concentration of TRPV1 decreases the concentration of TRPV1 by about 1%, about 2%, about 3%, about 4%, about 5%, about 10%, about 15% or more. In some embodiments, an agent that decreases TRPV1 concentration also modulates PGE2 signaling.

In some embodiments, an agent that decreases TRPV1 concentration is present in a composition as described herein in an amount of about 30% to about 100% w/w of the composition. For example, an agent that decreases TRPV1 concentration can be present in a composition as described herein in an amount of about 30% to about 40%, about 30% to about 50%, about 30% to about 60%, about 30% to about 70%, about 30% to about 80%, about 30% to about 90%, about 90% to about 100%, about 80% to about 100%, about 70% to about 100%, about 60% to about 100%, about 50% to about 100%, about 40% to about 100%, or about 50% to about 100%, w/w of the composition.

In some embodiments, an agent that decreases TRPV1 concentration is a flavone. In some embodiments, an agent that decreases TRPV1 concentration is a flavanone.

Agents that Decrease Calcitonin Gene-Related Peptide (CGRP) Concentration

In some embodiments, a composition as described herein can comprise an agent that decreases the concentration of CGRP. For example, in some embodiments, an agent that decreases the concentration of CGRP is an agent that decreases CGRP synthesis. As another example, an agent that decreases the concentration of CGRP can be an agent that decreases CGRP expression. Many agents that decrease the concentration of CGRP are known to one of skill in the art. Non-limiting examples of an agent that decreases the concentration of CGRP include hesperidin and apigenin. Several methods for measuring CGRP concentration are known to one of ordinary skill in the art. Non-limiting examples of such methods include: measuring CGRP protein using Western blot (see, for example, Yang et al. *Mol Med Rep.* 2018 April; 17(4): 5168-5174, which is incorporated by reference herein in its entirety).

In some embodiments, an agent that decreases the concentration of TRPV1 decreases the concentration of CGRP by at least 0.5%, 1%, 5%, 10%, or 15%. For example, the agent that decreases the concentration of CGRP decreases the concentration of CGRP by about 1%, about 2%, about 3%, about 4%, about 5%, about 10%, about 15% or more. In some embodiments, an agent that decreases CGRP concentration also modulates $PGE_2$ signaling.

In some embodiments, an agent that decreases CGRP concentration is present in a composition as described herein in an amount of about 30% to about 100% w/w of the composition. For example, an agent that decreases CGRP concentration can be present in a composition as described herein in an amount of about 30% to about 40%, about 30% to about 50%, about 30% to about 60%, about 30% to about 70%, about 30% to about 80%, about 30% to about 90%, about 90% to about 100%, about 80% to about 100%, about 70% to about 100%, about 60% to about 100%, about 50% to about 100%, about 40% to about 100%, or about 50% to about 100%, w/w of the composition.

In some embodiments, an agent that decreases CGRP concentration is a flavone. In some embodiments, an agent that decreases CGRP concentration is a flavanone.

Flavones and Flavanones

In some embodiments, a composition as described herein includes a flavone that modulates PGE2 signaling. In some embodiments, a composition as described herein includes a flavone that decreases COX-2 concentration and/or decreases prostaglandin $E_2$ ($PGE_2$) concentration. In some embodiments, a composition as described herein includes a flavone that modulates arachidonic acid metabolism.

As described herein, a "flavone" refers to a molecule derived from the oxidation of a flavan to form a phenylbenzopyranone motif. For example, a flavone is based on following structure (I).

Structure (I)

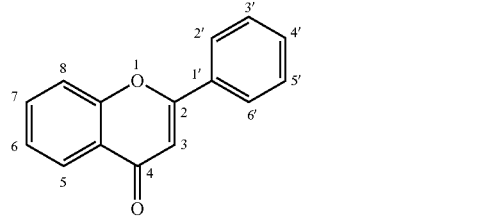

Non-limiting examples of flavones include trihydroxyflavones, hydroxyflavones, and flavone esters. Examples of a trihydroxyflavone include, without limitation, apigenin, baicalein, norwogonin, and galangin.

In some embodiments, a composition as described herein includes a flavone present in an amount of about 0.01% to about 50% w/w of the composition. For example, about 0.01% to about 5%, about 0.01% to about 10%, about 0.01% to about 15%, about 0.01% to about 20%, about 0.01% to about 25%, about 0.01% to about 30%, about 0.01% to about 35%, about 0.01% to about 40%, about 0.01% to about 45%, about 45% to about 50%, about 40% to about 50%, about 35% to about 50%, about 30% to about 50%, about 25% to about 50%, about 20% to about 50%, about 15% to about 50%, about 10% to about 50%, or about 5% to about 50% w/w of the composition. In some embodiments, a flavone is present in an amount of about 1% to about 20% w/w or about 2% to about 10% w/w of the composition. In some embodiments, a flavone is present in an amount of about 0.01% to about 10% w/w of the composition. For example, about 0.01% to about 1%, about 0.01% to about 2%, about 0.01% to about 3%, about 0.01% to about 4%, about 0.01% to about 5%, about 0.01% to about 6%, about 0.01% to about 7%, about 0.01% to about 8%, about 0.01% to about 9%, about 9% to about 10%, about 8% to about 10%, about 7% to about 10%, about 6% to about 10%, about 5% to about 10%, about 4% to about 10%, about 3% to about 10%, about 2% to about 10%, or about 1% to about 10% w/w of the composition. In some embodiments, a flavone is present in an amount of about 1% to about 5%, about 2% to about 4%, about 1% to about 4%, or about 2% to about 5% w/w of the composition. In some embodiments, a flavone is present in an amount of about 0.01%, about 0.05%, about 0.1%, about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, or about 10% w/w of the composition.

In some embodiments, the flavone is a trihydroxyflavone. In some embodiments, the trihydroxyflavone is selected from the group consisting of: apigenin, baicalein, norwogonin, galangin, and a combination thereof.

In some embodiments, the flavone is apigenin. In some embodiments, apigenin is present in an amount of about 0.01% to about 50% w/w of the composition. For example, about 0.01% to about 5%, about 0.01% to about 10%, about 0.01% to about 15%, about 0.01% to about 20%, about 0.01% to about 25%, about 0.01% to about 30%, about 0.01% to about 35%, about 0.01% to about 40%, about 0.01% to about 45%, about 45% to about 50%, about 40% to about 50%, about 35% to about 50%, about 30% to about 50%, about 25% to about 50%, about 20% to about 50%, about 15% to about 50%, about 10% to about 50%, or about 5% to about 50% w/w of the composition. In some embodiments, apigenin is present in an amount of about 1% to about 20% w/w or about 2% to about 10% w/w of the composition. In some embodiments, apigenin is present in an amount of about 0.01% to about 10% w/w of the composition. For example, about 0.01% to about 1%, about 0.01% to about 2%, about 0.01% to about 3%, about 0.01% to about 4%, about 0.01% to about 5%, about 0.01% to about 6%, about 0.01% to about 7%, about 0.01% to about 8%, about 0.01% to about 9%, about 9% to about 10%, about 8% to about 10%, about 7% to about 10%, about 6% to about 10%, about 5% to about 10%, about 4% to about 10%, about 3% to about 10%, about 2% to about 10%, or about 1% to about 10% w/w of the composition. In some embodiments, apigenin is present in an amount of about 1% to about 5%, about 2% to about 4%, about 1% to about 4%, or about 2% to about 5% w/w of the composition. In some embodiments, apigenin is present in an amount of about 0.01%, about 0.05%, about 0.1%, about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, or about 10% w/w of the composition.

In some embodiments, a composition as described herein includes a flavanone that can modulate $PGE_2$ signaling. In some embodiments, a composition as described herein includes a flavanone that decreases COX-2 concentration and/or decreases $PGE_2$ concentration. In some embodiments, a composition as described herein includes a flavanone that modulates arachidonic acid metabolism. In some embodiments, a composition as described herein includes a flavanone that modulates the oxidative stress pathway. In some embodiments, a composition as described herein includes a flavanone that decreases CGRP concentration.

A "flavanone" as used herein refers to a derivative of flavone and, unlike a flavone, the bond between positions 2 and 3 is saturated in a flavanone. Non-limiting examples of flavanone include a trihydroxyflavanone. Examples of a trihydroxyflavanone include, without limitation, hesperidin, butin, garbanzol, naringenin, and pinobanksin.

In some embodiments, a flavanone is present in an amount of about 30% to about 99% w/w of the composition. For example, about 30% to about 40%, about 30% to about 50%, about 30% to about 60%, about 30% to about 70%, about 30% to about 80%, about 30% to about 90%, about 90% to about 99%, about 80% to about 99%, about 70% to about 99%, about 60% to about 99%, about 50% to about 99%, about 40% to about 99%, about 50% to about 98%, or about 70% to about 98% w/w of the composition. In some embodiments, the flavanone is present in an amount of about 90% to about 99.5% w/w of the composition. For example, about 90% to about 91%, about 90% to about 92%, about 90% to about 93%, about 90% to about 94%, about 90% to about 95%, about 90% to about 96%, about 90% to about 97%, about 90% to about 98%, about 99% to about 99.5%, about 98% to about 99.5%, about 97% to about 99.5%, about 96% to about 99.5%, about 95% to about 99.5%, about 94% to about 99.5%, about 93% to about 99.5%, about 92% to about 99.5%, or about 91% to about 99.5% w/w of the composition. In some embodiments, the flavanone is present in an amount of about 90%, about 90.5%, about 91%, about 91.5%, about 92%, about 92.5%, about 93%, about 93.5%, about 94%, about 94.5%, about 95%, about 95.5%, about 96%, about 96.5%, about 97%, about 97.5%, about 98%, about 98.5%, about 99%, or about 99.5% w/w of the composition.

In some embodiments, the flavanone is a trihydroxyflavanone. In some embodiments, the trihydroxyflavanone is selected from the group consisting of: hesperidin, butin, garbanzol, naringenin, pinobanksin, and a combination thereof.

In some embodiments, the flavanone is hesperidin. In some embodiments, hesperidin is present in an amount of about 30% to about 99% w/w of the composition. For example, about 30% to about 40%, about 30% to about 50%, about 30% to about 60%, about 30% to about 70%, about 30% to about 80%, about 30% to about 90%, about 90% to about 99%, about 80% to about 99%, about 70% to about 99%, about 60% to about 99%, about 50% to about 99%, about 40% to about 99%, about 50% to about 98%, or about 70% to about 98% w/w of the composition. In some embodiments, hesperidin is present in an amount of about 90% to about 99.5% w/w of the composition. For example, about 90% to about 91%, about 90% to about 92%, about 90% to about 93%, about 90% to about 94%, about 90% to about 95%, about 90% to about 96%, about 90% to about 97%, about 90% to about 98%, about 99% to about 99.5%, about 98% to about 99.5%, about 97% to about 99.5%, about 96% to about 99.5%, about 95% to about 99.5%, about 94% to about 99.5%, about 93% to about 99.5%, about 92% to about 99.5%, or about 91% to about 99.5% w/w of the composition. In some embodiments, hesperidin is present in an amount of about 90%, about 90.5%, about 91%, about 91.5%, about 92%, about 92.5%, about 93%, about 93.5%, about 94%, about 94.5%, about 95%, about 95.5%, about 96%, about 96.5%, about 97%, about 97.5%, about 98%, about 98.5%, about 99%, or about 99.5% w/w of the composition.

Dietary Supplemental Compositions

The present disclosure provides compositions (e.g., dietary supplements) containing two or more agents that decrease the concentration of cyclooxygenase-2, decrease the concentration of transient receptor potential cation channel subfamily V member 1 (TRPV1), decrease calcitonin gene-related peptide concentration (CGRP), or a combination thereof. For example, in some embodiments, the present disclosure provides a compositions comprising two or more agents that decrease the concentration of cyclooxygenase-2 (COX-2). As another example, in some embodiments, the present disclosure provides a composition comprising two or more agents that decrease the concentration of TRPV1; decrease the concentration of CGRP; or a combination thereof. In some embodiments, the present disclosure provides compositions comprising a flavone and a flavanone. Such compositions can be used to relieve joint pain and joint inflammation. In addition, the disclosure provides methods for relieving or reducing joint pain or joint inflammation. Such methods involve the administration of a composition as provided herein.

In some embodiments, a composition as described herein includes two or more agents that decrease the concentration of COX-2. In some embodiments, at least one of the agents that decreases the concentration of COX-2 also decreases $PGE_2$ concentration. In some embodiments, at least one of the agents that decreases the concentration of COX-2 also decreases ROS concentration. In some embodiments, at least one of the agents that decreases COX-2 decreases COX-2 synthesis. In some embodiments, at least one of the agents that decreases COX-2 decreases COX-2 expression. In some embodiments, the two or more agents that decrease COX-2 concentration include a flavone and a flavanone.

In some embodiments, a composition as described herein includes two or more agents that decrease the concentration of transient receptor potential cation channel subfamily V member 1 (TRPV1); decrease the concentration of calcitonin gene-related peptide (CGRP); or a combination thereof. In some embodiments, the agent that decreases the concentration of TRPV1 modulates $PGE_2$ signaling. In some embodiments, the agent that decreases the concentration of CGRP modulates $PGE_2$ signaling. In some embodiments, the agent that decreases TRPV1 concentration includes a flavone, a flavanone, or a combination thereof. In some embodiments, the agent that decreases CGRP concentration includes a flavone, a flavanone, or a combination thereof.

In some embodiments, a composition as described herein includes a flavone and a flavanone. In some embodiments, the composition comprises: about 0.01% to about 30% w/w of the composition of flavanone; and about 30% to about 99% w/w of the composition of flavone. In some embodiments, the composition comprises: about 1% to about 5% w/w of the composition of flavanone; and about 95% to about 99% w/w of the composition of flavone. In some embodiments, the composition comprises: about 3% w/w of the composition of flavanone; and about 97% w/w of the composition of flavone. In some embodiments, the flavone is apigenin. In some embodiments, the flavanone is hesperidin.

In some embodiments, the composition comprises: about 0.01% to about 30% w/w of the composition of a flavone; and about 30% to about 99% w/w of the composition of a flavanone. In some embodiments, the composition comprises: about 1% to about 5% w/w of the composition of a flavone; and about 90% to about 99% w/w of the composition of a flavanone. In some embodiments, the composition comprises: about 3% w/w of the composition of a flavone; and about 97% w/w of the composition of a flavanone.

In some embodiments, a composition as described herein comprises hesperidin and apigenin. For example, in some embodiments, the composition comprises: about 0.01% to about 30% w/w of the composition of apigenin; and about 30% to about 99% w/w of the composition of hesperidin. In some embodiments, the composition comprises: about 1% to about 5% w/w of the composition of apigenin; and about 90% to about 99% w/w of the composition of hesperidin. In some embodiments, the composition comprises: about 3% w/w of the composition of apigenin; and about 97% w/w of the composition of hesperidin.

In some embodiments, the composition includes a flavone and a flavanone at a ratio of about 1:1000, about 1:500, about 3:1000, about 1:250, about 1:200, about 3:500, about 7:1000, about 1:125, about 9:1000, about 1:100, about 1:50, about 3:100, about 1:25, about 1:20, about 3:50, about 7:100, about 2:25, about 9:100, or about 1:10 flavone:flavanone. In some embodiments, the composition includes a flavone and a flavanone at a ratio of about 3:100 flavone:flavanone.

In some embodiments, a composition as described herein includes hesperidin and apigenin. In some embodiments, the composition comprises: about 1% to about 5% w/w of the composition of apigenin; and about 95% to about 99% w/w of the composition of hesperidin. In some embodiments, the composition comprises: about 0.01% to about 30% w/w of the composition of apigenin; and about 30% to about 99% w/w of the composition of hesperidin. In some embodiments, the composition comprises: about 3% w/w of the composition of apigenin; and about 97% w/w of the composition of hesperidin.

In some embodiments, the composition includes apigenin and hesperidin at a ratio of about 1:1000, about 1:500, about 3:1000, about 1:250, about 1:200, about 3:500, about 7:1000, about 1:125, about 9:1000, about 1:100, about 1:50, about 3:100, about 1:25, about 1:20, about 3:50, about 7:100, about 2:25, about 9:100, or about 1:10 apigenin:hesperidin. In some embodiments, the composition includes a flavanone and a flavone at a ratio of about 3:100 apigenin:hesperidin.

In some embodiments, a composition as described herein is formulated for oral delivery. A composition as described herein can be formulated for oral delivery in a variety of ways. For example, the composition can be in the form of a tablet or powder. As another example, a composition as described herein can be in the form of a liquid, solution, suspension, gummy, tablet, powder, soft gelatin capsules, or hard gelatin capsules. Commercial dietary supplements are generally formulated for oral administration. For oral administration, tablets or capsules can be prepared by conventional means with pharmaceutically acceptable excipients such as binding agents, fillers, lubricants, disintegrants, or wetting agents. The tablets can be coated by methods known in the art. Liquid preparations for oral administration can take the form of, for example, solutions, syrups, or suspension, or they can be presented as a dry product for constitution with saline or other suitable liquid vehicle before use. For example, a composition as described herein can be presented as dry powder and dissolved in a suitable liquid carrier. In some embodiments, a composition as described herein can be diluted in a suitable liquid carrier. In some embodiments, a composition as described herein is diluted in an energy drink. In some embodiments, liquid preparations also can contain pharmaceutically acceptable additives such as suspending agents, emulsifying agents, non-aqueous vehicles, preservatives, buffer salts, flavoring agents, coloring agents, and sweetening agents as appropriate. In some embodiments, a composition as described herein can be presented as a stick pack. Preparations for oral administration can be suitably formulated to give controlled release of the compound.

Tablets and powders can be configured to have a unit dosage equal to the daily desired dosage. For example, if a subject desires 1000 mg of a particular composition, each tablet can be 1000 mg in weight. As another example, if a subject desires 1000 mg of a particular composition each tablet can be 500 mg in weight and the subject can take two tablets. The dosages of a particular composition will depend on many factors including the mode of administration. As an example, a composition as described herein can be formulated in a dose such that an individual receives the amounts as shown in Table 1, e.g., in a single tablet, divided among 2 or more tablets, or as a powder.

TABLE 1

| Components | Dosage Amount (mg) | Weight Percentage |
| --- | --- | --- |
| Apigenin | 30 | 3% |
| Hesperidin | 1000 | 97% |

In addition, a composition provided herein can contain a pharmaceutically acceptable carrier for in vivo administration to a subject. In some embodiments, the weight percentages of a flavone and a flavanone as provided herein account for the active agent portion of a composition described herein. For example, in some embodiments, if one or more pharmaceutically acceptable carriers are present, the weight percentage for the active agent portion is based on the amounts of the flavone and flavanone and does not include the weight percentages of the pharmaceutically acceptable carrier(s). In some embodiments, a composition provided herein contains apigenin and hesperidin present in the dosage amount and/or weight percentage (e.g., the weight percentage for the active agent portion) as shown in Table 1, and further includes a pharmaceutically acceptable carrier.

Such pharmaceutically acceptable carriers include, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include water, alcohol, saline, and buffered solutions. Pharmaceutically acceptable carriers also can include physiologically acceptable aqueous vehicles (e.g., physiological saline) or other known carriers appropriate to specific routes of administration. Preservatives, flavorings, and other additives such as, for example, proteins, antimicrobials, chelating agents, inert gases, and the like also can be present in a composition.

Methods

Also provided herein are methods for decreasing joint inflammation in a subject in need thereof comprising administering to the subject any of the compositions as described herein. Also provided herein are methods for improving joint inflammation in a subject in need thereof comprising administering to the subject any of the compositions as described herein.

In some embodiments, the joint inflammation is associated with one or more of: an injury, ankylosing spondylitis, bursitis, gout, juvenile rheumatoid arthritis, lupus, Lyme disease, osteoarthritis, pseudogout, psoriatic arthritis, rheumatoid arthritis, and tendonitis. In some embodiments, an injury can include a broken bone, a dislocation (e.g., a luxation or a subluxation), a sprain, or a strain.

In some embodiments, the inflamed joint is a foot joint, a knee joint, a hip joint, a sacroiliac joint, a temporomandibular joint, a facet joint, a sternoclavicular joint, a shoulder joint, an acromioclavicular joint, a wrist joint (e.g., a radiocarpal joint, a intercarpal joint, a midcarpal joint), an elbow joint, a carpometacarpal joint, an intermetacarpal articulation, a metacarpophalangeal joint, or an interphalangeal joint of the hand.

In some embodiments, the composition is administered orally.

Also provided herein are methods for decreasing joint pain in a subject in need thereof comprising administering to the subject any of the compositions as described herein.

In some embodiments, the joint pain is associated with one or more of: an injury, adult Still's disease, ankylosing spondylitis, avascular necrosis (e.g., death of bone tissue due to limited blood flow), bone cancer, bursitis, complex regional pain syndrome (e.g., chronic pain due to a dysfunctional nervous system), fibromyalgia, gonococcal arthritis, gout (e.g., arthritis related to excess uric acid), hypothyroidism, juvenile idiopathic arthritis, leukemia, lupus, Lyme disease, osteoarthritis, osteomyelitis, Paget's disease of bone, polymyalgia rheumatic, pseudogout, psoriatic arthritis, reactive arthritis, rheumatic fever, rheumatoid arthritis, rickets, sarcoidosis, septic arthritis, and tendinitis. In some embodiments, an injury can include a broken bone, a dislocation (e.g., a luxation or a subluxation), a sprain, or a strain.

In some embodiments, the painful joint is a foot joint (e.g., an ankle joint, a subtalar joint, an interphalangeal joints of the foot), a knee joint, a hip joint, a sacroiliac joint, a temporomandibular joint, a facet joint, a sternoclavicular joint, a shoulder joint, an acromioclavicular joint, a wrist joint (e.g., a radiocarpal joint, a intercarpal joint, a midcarpal joint), an elbow joint, a carpometacarpal joint, an intermetacarpal articulation, a metacarpophalangeal joint, or an interphalangeal joint of the hand.

In some embodiments, the joint pain is measured using the Visual Analog Scale (VAS) Pain Score (see, e.g., Delgado et al. J. Am. Acad. Orthop. Surg. Glob. Res. Rev. 2018 Mar. 23; 2(3): e088, which is incorporated by reference herein). In some embodiments, the joint pain of the subject improves after administration of composition A as compared to before administration of composition A, e.g., as measured using the VAS Pain Score. For example, in some embodiments, the VAS Pain Score of the subject is decreased after administration of composition A as compared to before administration of composition A.

In some embodiments, the composition is administered orally.

EXAMPLES

Example 1. In Silico Simulations of Compositions for Joint Pain and Inflammation Protocol The in silico simulations were performed using CytoSolve®, a commercially available tool that enables the computational modeling of biomolecular pathways. CytoSolve® can scale and model highly complex biomolecular phenomena by its ability to integrate and couple the computations of smaller biomolecular pathways (see, e.g., Ayyadurai and Forbes-Dewey Jr. *Cellular and Molecular Bioengineering.* 2011, 4(1):28-45; Nordsletten. *IEEE Trans Biomed Eng.* 2011; 58(12):3508-12; Ayyadurai and Deonikar. *Agricultural Sciences.* 2015; 6:630-662; Ayyadurai. *Commun Med Care Compunetics.* 2011; 1:115-168; Koo et al. *Biophys J.* 2013; 104(10):2295-306; Sweeney et al. *Nat Neurosci.* 2016; 19(6):771-83; and Ayyadurai. (2007) Scalable Computational Architecture for Integrating Biological Pathway Models (Doctoral Dissertation, Massachusetts Institute of Technology); each of which is hereby incorporated by reference in its entirety).

Results

FIG. 1 was derived using CytoSolve® to model mechanisms of calcitonin gene-related peptide (CGRP) signaling. Once these pathways were integrated using CytoSolve®, the resulting biomolecular computational model was used to identify the ranges of concentrations of apigenin and hesperidin that elicit a synergistic effect on the biomarker, CGRP (see Table 2). The amounts of apigenin and hesperidin from Table 2 were used to model the effect on CGRP of each alone versus the control (0.045 nm).

Figure 2:
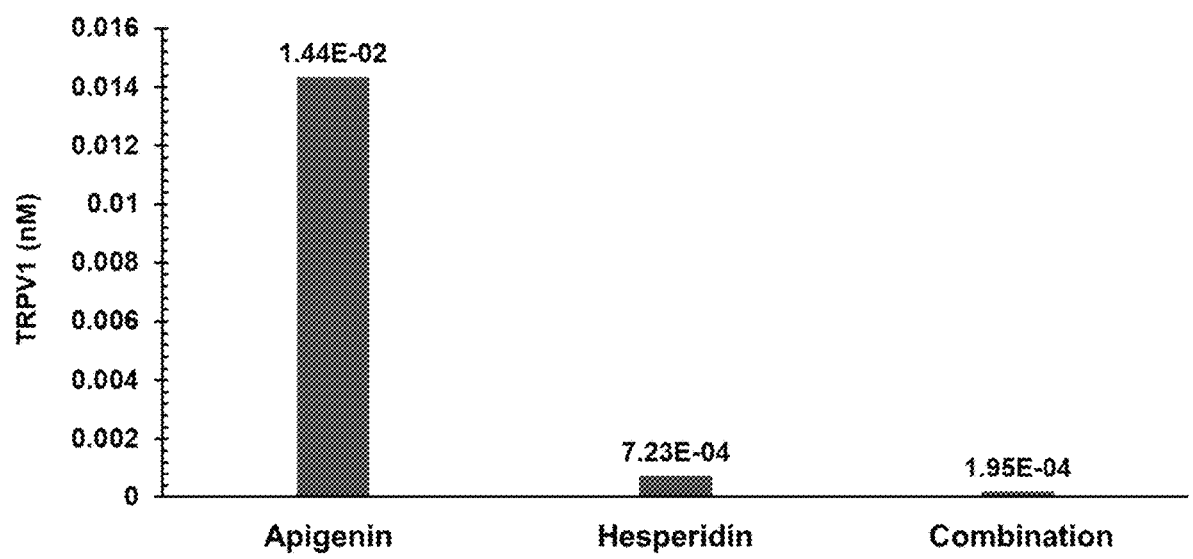
FIG. 2 is a bar graph comparing the concentration of transient receptor potential cation channel subfamily V member 1 (TRPV1) for apigenin, hesperidin, and a combination of apigenin and hesperidin versus a control (data not shown, the concentration of TRPV1 for the control was 0.039 nM). The plot is based on a biomolecular computational model using CytoSolve® and modeling mechanisms of the TRPV1 signaling pathway.

FIG. 2 was derived using CytoSolve® to model mechanisms of transient receptor potential cation channel subfamily V member 1 ($TRPV_1$) signaling. Once these pathways were integrated using CytoSolve®, the resulting biomolecular computational model was used to identify the ranges of concentrations of apigenin and hesperidin that elicit a synergistic effect on the biomarker, $TRPV_1$. The amounts of apigenin and hesperidin from Table 2 were used to model the effect on $TRPV_1$ versus the control (0.039 nM).

Figure 3:
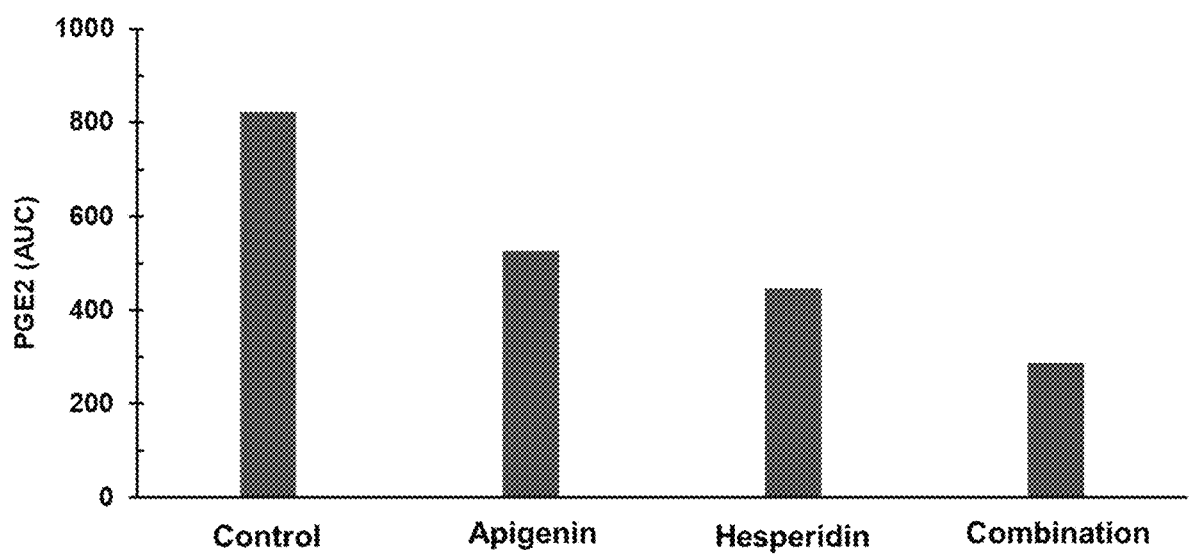
FIG. 3 is a bar graph comparing the AUC of prostaglandin $E_2$ ($PGE_2$) levels for apigenin, hesperidin, and a combination of apigenin and hesperidin versus a control. The plot is based on a biomolecular computational model using CytoSolve® and modeling mechanisms of the arachidonic acid metabolism pathway.

FIG. 3 was derived by using CytoSolve® to model mechanisms of arachidonic acid metabolism. Once these pathways were integrated using CytoSolve®, the resulting biomolecular computational model was used to identify the ranges of concentrations of apigenin and hesperidin that elicit a synergistic effect on the biomarker, prostaglandin $E_2$ ($PGE_2$). The amounts of apigenin and hesperidin from Table 2 were used to model the effect on PEG2 versus the control.

Figure 4:
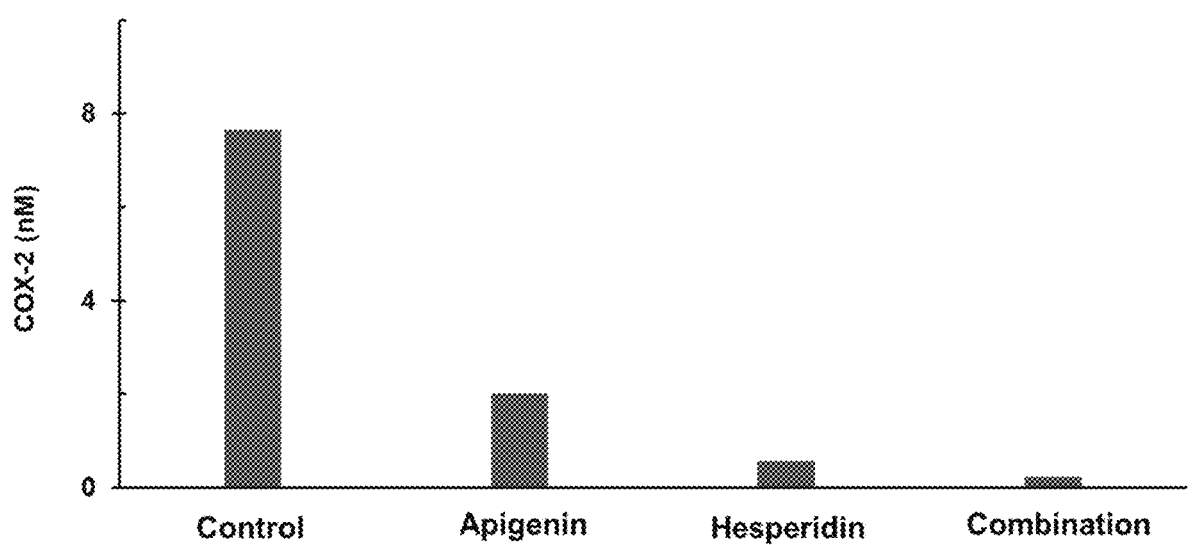
FIG. 4 is a bar graph comparing the concentration of COX-2 for apigenin, hesperidin, and a combination of apigenin and hesperidin versus a control. The plot is based on a biomolecular computational model using CytoSolve® and modeling mechanisms of COX-2 synthesis pathway.

FIG. 4 was derived using CytoSolve® to model mechanisms of cyclooxygenase-2 (COX-2) synthesis. Once these pathways were integrated using CytoSolve®, the resulting biomolecular computational model was used to identify the ranges of concentrations of apigenin and hesperidin that elicit a synergistic effect on the biomarker, COX-2. The amounts of apigenin and hesperidin from Table 2 were used to model the effect on COX-2 versus the control.

Figure 5:
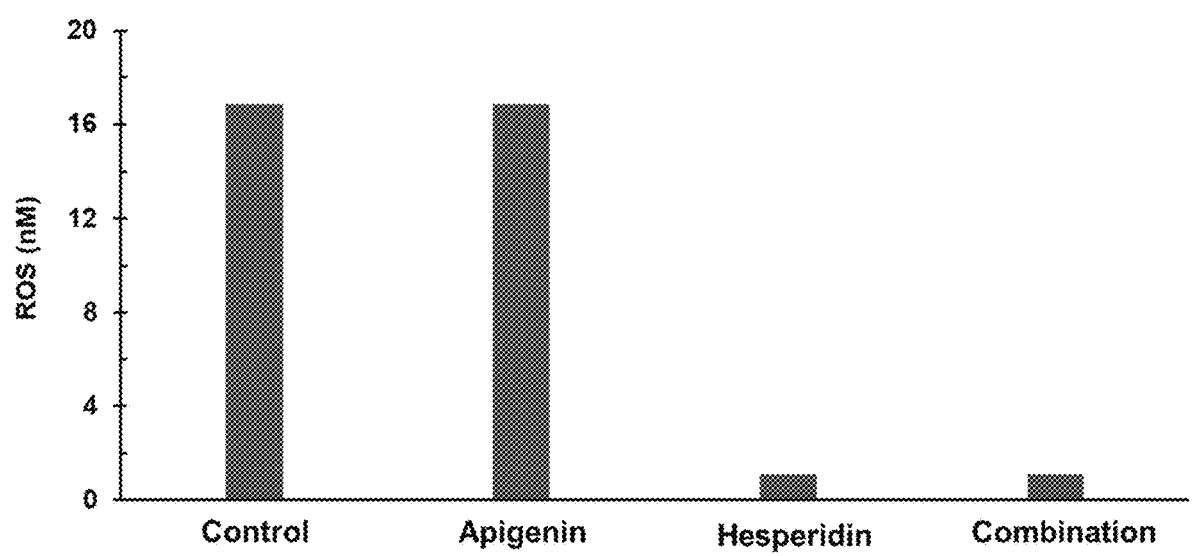
FIG. 5 is a bar graph comparing the concentration of reactive oxygen species (ROS) for apigenin, hesperidin, and combination versus a control. The plot is based on a biomolecular computational model using CytoSolve® and modeling mechanisms of oxidative stress pathway.

FIG. 5 was derived by using CytoSolve® to model mechanisms of oxidative stress. Once these pathways were integrated using CytoSolve®, the resulting biomolecular computational model was used to identify the ranges of concentrations of apigenin and hesperidin that elicit a synergistic effect on the biomarker, reactive oxygen species (ROS), see Table 2. The amounts of apigenin and hesperidin from Table 2 were used to model the effect on ROS versus the control and combination.

TABLE 2

| Components | Dosage Amount (mg) | Weight Percentage (%) |
|---|---|---|
| Apigenin | 30 | 3% |
| Hesperidin | 1000 | 97% |

Example 2. In Vivo Efficacy Testing of Compositions for Inflammation

Protocol

The in vitro efficacy testing of a joint pain and inflammation composition (Composition A; see Table 2 in Example 1) on inflammation are conducted using primary cell culture of human chondrocytes as described in Wu et al., 2020 (see, e.g., Wu et al. *Regenerative Therapy.* 2020; 14; 177-183, which is incorporated by reference herein in its entirety). Experiments are conducted with and without the application of Composition A. COX-2 and $PGE_2$ are measured in the cell culture as an indicator of inflammation. Samples from cell culture re withdrawn and tested for COX-2 mRNA using RT-PCR or Northern blot; COX-2 protein using Western blot (see, for example, Inoue et al. BMC Urol. 2013 Jan. 5; 13:1; Hirata et al. Anticancer Res. 2005 September-October; 25(5):3367-74; and Gordillo-Moscoso et al. Lipids Health Dis. 2013 May 3; 12:62; each of which are incorporated by reference herein in their entireties); and $PGE_2$ protein using ELISA (see, for example, Wang et al. *PLoS One.* 2017; 12(5): e0177166; which is incorporated by reference herein in its entirety).

Expected Results

Comparison of COX-2 and $PGE_2$ levels in the cell culture with and without application of Composition A is performed to determine the efficacy of Composition A.

Example 3. In Vitro Efficacy Testing of Compositions for Joint Pain

Protocol

The in vitro efficacy testing of Composition A on pain is conducted using primary cell culture of dorsal root of spinal nerve as described in Yang et al., 2018 (see, e.g., Yang et al. *Mol Med Rep.* 2018 April; 17(4): 5168-5174, which is incorporated by reference herein in its entirety). Experiments are conducted with and without the application of Composition A. TRPV1 and CGRP will be measured in the cell culture as an indicator of pain. Samples from cell culture are withdrawn and tested for TRPV1 mRNA using RT-qPCR or Northern blot (see, for example, Yang et al. *Mol Med Rep.* 2018 April; 17(4): 5168-5174, which is incorporated by reference herein in its entirety) and CGRP protein using Western blot (see, for example, Yang et al. *Mol Med Rep.* 2018 April; 17(4): 5168-5174, which is incorporated by reference herein in its entirety).

Expected Results

Comparison of TRPV1 and CGRP levels in the cell culture with and without application of Composition A is performed to determine the efficacy of Composition A.

Example 4. Reducing Pain, Inflammation, Stiffness, and Discomfort Using Compositions for Joint Pain and Inflammation A 56 year old male subject with history of chronic back pain (pain level to be 6 or above on a scale of 1 to 10) resulting from multiple spinal cord surgeries ingested two (2) capsules of Composition A on Apr. 11, 2020. The formulation of capsules was as described in Example 1. The capsules were taken in the morning. The subject reported a significant drop in pain level to 1 to 2 within 1.5 hours of ingestion of the two capsules. The subject continues to take two (2) capsules per day and has reported improved quality of life due to continued alleviation of pain and was able to completely replace over-the-counter non-steroidal anti-inflammatory pain relievers with Composition A capsules.

Example 5. Reducing Swelling, Stiffness, and Discomfort Using Compositions for Joint Pain and Inflammation A 27-year-old quarter horse mare with major swelling and arthritis in both front ankles was given a liquid suspension of Composition A. The formulation of liquid suspension based on the weight percentages shown in Example 1 and was administered in the morning. A significant drop in swelling of both ankle joints was reported within two hours of administration of the suspension of Composition A. By the end of the first day, a reduction in stiffness of the two joints and a significant improvement the free movement of the animal was observed. Improved stool consistency was observed after administration of Composition A, which could be attributed to discontinuation of non-steroidal anti-inflammatory (NSAID) pain reliever, which were prescribed to the animal. The animal was administered Composition A once a day and showed improvement in stiffness, lack of swelling of the ankle joints, and improved movement in the legs.

Example 6. Clinical Efficacy Testing of Compositions on Pain and Inflammation

Protocol

Clinical efficacy studies are conducted for Composition A using up to 100 subjects over a period of four (4) week. The clinical study protocol is described below.

Study Group Selection
1. Inclusion Criteria
   a. Age group: Adult population in the age group of ≥18 y
   b. Gender: Male and female (females should be on birth control)
   c. Education: Should be undertaking full-time post-secondary training at a four-year or two-year college
   d. Inclusion criteria test: The Visual Analog Scale (VAS) Pain Score (see, e.g., Delgado et al. *J. Am. Acad. Orthop. Surg. Glob. Res. Rev.* 2018 Mar. 23; 2(3): e088, which is incorporated by reference herein)
2. Exclusion criteria:
   a. Individuals with high VAS pain scores (e.g. >5 on the scale of 1-10)
   b. Pregnant or nursing individuals
   c. Individuals with chronic illness
   d. Individuals receiving prescription medication
   e. Individuals taking other joint health supplements Study Type Selection
  Placebo-controlled Randomized clinical study: Random allocation to either the group receiving the supplement under investigation or to a group receiving placebo treatment as the control
Study Design Type
  Parallel-group: Each participant is randomly assigned to a group, and all the participants in the group receive (or do not receive) Composition A
Outcome Measurements
  1. Will be based on the Visual Analog Scale (VAS) Pain Score
  2. Will include primary outcome and secondary outcome
  3. Can be self-monitored questionnaire (or a smartphone app) or reported by people who know the individual participating in the study
Results
  Results obtained from the clinical study are analyzed to determine efficacy of Composition A using the following steps:
  1. Appropriate statistical tests are performed to estimate the change levels in the 95% confidence interval for the two study groups where the outcome measure is in the form of ordinal level scale. Examples of such tests include:
    a. Wilcoxson Rank-Sum test; and
    b. Mann-Whiney U test
  2. Perform an intention-to-treat (ITT) analysis to overcome the issue arising from dropouts i.e. "Attrition bias."

Other Embodiments

It is to be understood that while the invention has been described in conjunction with the detailed description thereof, the foregoing description is intended to illustrate and not limit the scope of the invention which is defined by the scope of the appended claims. Other aspects, advantages, and modification are within the scope of the following claims.

What is claimed is:

1. A method for decreasing joint inflammation in a subject in need thereof comprising administering to the subject a composition comprising two agents that decrease the concentration of cyclooxygenase-2 (COX-2), wherein the two agents that decrease COX-2 concentration are apigenin and hesperidin, and the composition comprises apigenin and hesperidin at a ratio of about 3:100 apigenin: hesperidin.

2. The method of claim 1, wherein the joint inflammation is associated with one or more of: an injury, ankylosing spondylitis, bursitis, gout, juvenile rheumatoid arthritis, lupus, Lyme disease, osteoarthritis, pseudogout, psoriatic arthritis, rheumatoid arthritis, and tendonitis.

3. The method of claim 1, wherein at least one agent that decreases the concentration of COX-2 also decreases one or more of:
  prostaglandin $E_2$ ($PGE_2$) concentration; the concentration of reactive oxygen species (ROS); and COX-2 expression.

4. The method of claim 1, wherein at least one agent that decreases the concentration of COX-2 modulates COX-2 synthesis.

5. The method of claim 3, wherein at least one agent that decreases the concentration of PGE2 modulates arachidonic acid metabolism.

6. The method of claim 3, wherein the at least one agent that decreases the concentration of ROS modulates an oxidative stress pathway.

7. A method for decreasing joint pain of a subject in need thereof comprising administering to the subject a composition comprising two agents that decrease the concentration of transient receptor potential cation channel subfamily V member 1 (TRPV1); decrease the concentration of calcitonin gene-related peptide (CGRP); or a combination thereof, wherein the two agents are apigenin and hesperidin, and the composition comprises apigenin and hesperidin at a ratio of about 3:100 apigenin: hesperidin.

8. The method of claim 7, wherein the joint pain is associated with one or more of: an injury, adult Still's disease, ankylosing spondylitis, avascular necrosis, bone cancer, bursitis, complex regional pain syndrome, fibromyalgia, gonococcal arthritis, gout, hypothyroidism, juvenile idiopathic arthritis, leukemia, lupus, Lyme disease, osteoarthritis, osteomyelitis, Paget's disease of bone, polymyalgia rheumatic, pseudogout, psoriatic arthritis, reactive arthritis, rheumatic fever, rheumatoid arthritis, rickets, sarcoidosis, septic arthritis, and tendinitis.

9. The method of claim 7, wherein at least one agent also modulates $PGE_2$ signaling.

\* \* \* \* \*